United States Patent [19]

Kusnetz et al.

[11] 4,199,260
[45] Apr. 22, 1980

[54] APPARATUS AND METHOD FOR DETERMINING THE CONCENTRATION IN A SAMPLE

[75] Inventors: Jacob Kusnetz, New City; Warren Groner, Whitestone, both of N.Y.

[73] Assignee: Technicon Instruments Corporation, Tarrytown, N.Y.

[21] Appl. No.: 935,411

[22] Filed: Aug. 21, 1978

[51] Int. Cl.² .................. G01N 21/48; G01N 31/08
[52] U.S. Cl. .................................. 356/411; 73/23.1
[58] Field of Search .................. 356/337–340, 356/342, 343, 410, 411, 432, 433, 435–437, 442; 250/573, 574, 578; 73/21.1, 61.1 C

[56] References Cited

U.S. PATENT DOCUMENTS 1,760,209  5/1930  Pfeiffer .................................. 356/135

Primary Examiner—John K. Corbin
Assistant Examiner—Bruce Young Arnold

Attorney, Agent, or Firm—S. P. Tedesco

[57] ABSTRACT

Apparatus and method for determining the concentration of a constituent in a sample using chromatographic and optical measuring techniques. A sample containing a constituent to be analyzed is fractionated by a chromatographic column. A light beam is passed through the constituent fraction in the column, and the light absorbance (or transmittance) is measured. The fluid carrier (or solvent) eluting through the column will generally increase the transmissivity of the light passing through the column due to a difference between the indices of refraction of the carrier fluid and the chromatographic packing material. Such increased transmissivity will generally offset any decrease in the transmittance due to trace amounts of the constituent in the sample. The optical measurement is compensated to nullify such increased transmissivity, so as to allow measurement of such trace amounts of constituents.

29 Claims, 5 Drawing Figures

APPARATUS AND METHOD FOR DETERMINING THE CONCENTRATION IN A SAMPLE

FIELD OF INVENTION

This invention relates to optical apparatus and method for measuring the concentrations of constituents in a sample which has been fractionated in a chromatographic column.

BACKGROUND OF THE INVENTION

Heretofore, it has been known to qualitatively determine the types of constituents in a sample to be analyzed by fractionating the sample using a chromatographic column. The fractions so obtained were then optically analyzed by scanning the fractions at various absorbance wavelengths, while being passed along the chromatographic column. A linear Beer's plot would then identify the type of substance in the sample.

Such a technique is described in "MOLECULAR SIEVE STUDIES OF INTERACTING PROTEIN SYSTEMS,"E. E. Brumbaugh and G. K. Ackers, Journal of Biological Chemistry, Vol. 243, No. 24, pp. 6315–6324, (1968) and "MOLECULAR SIEVE STUDIES OF INTERATING PROTEIN SYSTEMS," E. E. Brumbaugh and G. K. Ackers, Analytical Biochemistry, Vol. 41, pp 543–559 (1971).

The present invention seeks to perform quantitative measurements with greater sensitivity of samples fractionated within a column by measuring the transmissivity of a light beam passing both through the column and one or more selected fractions of the sample.

When the prior art technique was used to quantitatively measure trace amounts of certain materials, it was discovered that the carrier fluid or the solvent passed through the chromatagraphic column increased the light transmissivity of the column. Such increased transmissivity was due to the difference in the respective indices of refraction of the fluid carrier and the chromotographic packing material. Such increased transmissivity, while small, would balance any decrease in transmissivity resulting from the trace amount of the constituent being analyzed. As a result, trace amounts of materials within a sample could not be measured, and, hence, the sensitivity of prior art systems was limited.

The present invention seeks to extend the sensitivity of chromatographic systems by nullifying (or compensating) the change in transmissivity due to the fluid carrier. Such compensation can be effected either optically or electronically.

SUMMARY OF THE INVENTION

The invention pertains to an apparatus and method for determining the concentration of a constituent in a sample. An optical measurement is obtained for light passing through a chromatographic column and that fraction of the sample containing the constituent being measured. The optical measurement is compensated by nullifying the optical effects due to the index of refraction of the fluid carrier within the column. The compensation is accomplished in two ways:

(a) The measured light is received at a prescribed angle to the directed light beam; the angle being related to the effect of the carrier fluid upon the column's effective index of refraction. This prescribed angle can be determined empirically, such that the increased transmissivity is compensated (or nullified) by a decreased scattered component of the light passed through the column, or (b) The light is measured at two positions about the column to obtain two light measurements, the first measurement preferably being made along the optical axis and the second measurement being made off the the optical axis, say 90° with respect to the optical axis. The first measurement will include the refractive effects of the carrier fluid, and the second measurement will include a quantum of the light scattered by the column. The first and second measurements are amplified such that, when summed electronically, the quantum of scattered light nullifies the refraction effects of the carrier fluid.

It is an object of this invention to provide an improved apparatus and method for determining the concentration of a constituent in a sample;

It is another object of the invention to provide an improved apparatus and method for increasing the sensitivity of an optical measuring system;

It is a further object of this invention to provide an optical apparatus and method for measuring trace amounts of a constituent in chromatographic systems;

It is still a further object of the invention to provide a chromatographic and optical apparatus and method for analyzing samples, wherein changes in the refractive index of the column due to the fluid carrier of the samples will be compensated.

DETAILED DESCRIPTION OF THE DRAWINGS

These and other objects of this invention will be better understood and will become more apparent with reference to the following detailed description taken in conjunction with the accompanying drawings, in which.

DETAILED DESCRIPTION

Figures 1, 2, 3:
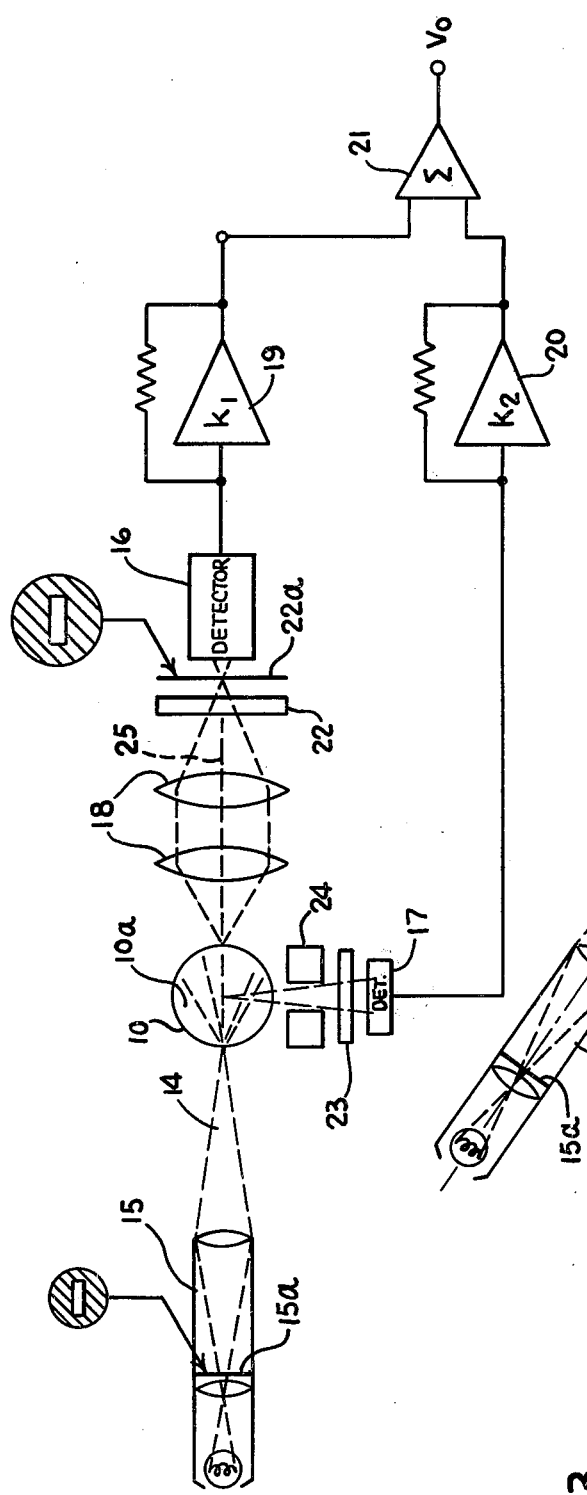
FIG. 1 is a schematic plan view of one embodiment of the apparatus of the invention.
FIG. 2 is a schematic plan view of a second embodiment of the apparatus of this invention.
FIG. 3 is a graph of electrical measurements illustrating the effects of the fluid solvent upon the light passing through the column of FIG. 1.

Generally speaking, the invention relates to apparatus and method for determining the concentration of a constituent within a sample, particularly where such constituent is present in only trace quantities. Referring to FIG. 1a, a chromatographic column 10 is shown, which contains, e.g., a gel 10a having a given index of refraction. A sample to be analyzed is introduced into the column 10, as depicted by arrow 11. The sample is fractionated by column 10, such that several bands or fractions 12 will be dispersed throughout the column. The sample is carried by a solvent which is pumped through the gel column by pump 13. A beam of light 14 of a known wavelength is directed through column 10 and a selected fraction 12, the light transmitted therethrough being passed through a collimating lens arrangement 18, an optical filter 22, and field stop 22a onto a detector 16. As is well known, the output of detector 16 is indicative of the concentration of the particular constituent under examination, as will be hereafter described more fully.

Figure 1A:
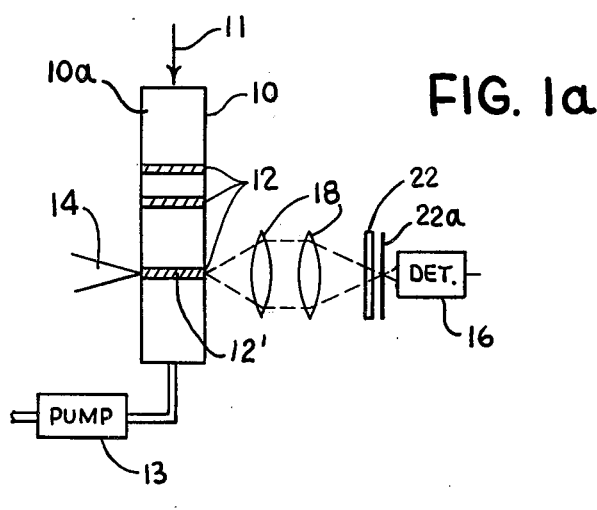
FIG. 1a is a schematic side view of a portion of the apparatus shown in FIG. 1.

Referring to FIG. 1, beam 14 is directed through the column 10 of FIG. 1a. The beam 14 is provided by the substantially collimated light source 15 and has a rectangular cross-section defined by aperture mask 15a. Two photodetectors 16 and 17, respectively, are positioned about the column 10 to measure the light passing through the column. Photodetector 16 is positioned along the optical axis 25 to detect transmitted light, and photodetector 17 is disposed at a right angle to the optical axis 25 to detect scattered light. A pair of lenses 18 focus the light to detector 16 through rectangular field stop 22a. A filter 22 is chosen to transmit light to detector 16 at a wavelength that will provide a peak in absorbance for the particular constituent in the fraction 12 to be measured. The detector 16 measures the transmissivity of the light which passes directly through column 10. The output of detector 16 is fed to an amplifier 19 having a gain $K_1$. The detector 17 measures light scattered by the column 10. An aperture 24 directs the light to a filter 23 which is chosen to transmit light at a wavelength of minimum absorbance of the particular fraction. This will provide a scattered light measurement that is solely a function of the fluid carrier. The output of detector 17 is fed to amplifier 20 having a gain $K_2$. The outputs of amplifiers 19 and 20 are respectively fed to a summing amplifier 21.

Normally, as described in the prior art, only a single detector, such as detector 16, would be used to measure the light absorbance of the fraction 12 under analysis. However, the present invention recognizes that the eluant (fluid carrier) of the sample will change the light absorbance reading, because it will cause the effective index of refraction of the column 10 to change. This is so, because the eluant will displace the gel solution which suspends the gel particles. Therefore, the effective index of refraction of the column actually becomes a composite of the gel material and the fluid carrier of the sample. The invention in one embodiment thereof, therefore, uses two detectors 16 and 17, respectively, to compensate for the light change due to the eluant. It has been realized that any increase in light transmission through the gel due to the eluant, will also provide a corresponding decrease in the scattered (diffused) light.

By measuring both the transmitted light and the scattered light, and electronically summing the output signals, it is possible to cancel or null the increase of transmitted light due to the eluant on one hand, with the decrease of scattered light due to the eluant on the other hand. Thus, it is possible by means of this invention to nullify the light effects influencing the determination of the concentration of the analyzed fraction 12. This technique is useful (with proper selection of filters 22 and 23, respectively) in measuring any one of the separated fractions 12 in the column 10. It should be appreciated that filters 22 and 23 can be substituted in phase with the passage of sample fractions through column 10, whereby selected constituents in one or more fractions can be measured, in turn.

More specifically, when investigating, for example, trace amounts of lysed hemoglobin in plasma, SEPHAROSE 4BCL (manufactured by Pharmacia, Piscatoway, N.J.), suspended in phosphate buffered saline, may be used as the gel material.

The degree of scattering and/or transmissivity of the light depends upon the relationship of the respective indices of refraction of the gel material, or particles, and the carrier fluid of the sample. The gel of the column is generally comprised of particles suspended in a fluid. Normally, for whole blood analysis, the fluid chosen for SEPHAROSE is 0.9% saline buffered solution with an index of refraction of 1.335 as compared to that of blood plasma whose index of refraction is 1.349. The index for blood plasma will vary somewhat with each particular blood sample, but these variations will not seriously effect the analysis. The plasma of the blood sample displaces the saline of the gel as it travels through column 10, and will change the gel's effective index of refraction.

As the total light energy remains constant, any decrease in scattered light will result in an increase in the transmitted light through the gel. FIG. 3 illustrates this phenomena. Curve "a" is a voltage output from amplifier 19, and shows an increase $\Delta V_T$ in the transmitted light $V_T$ due to the plasma, as measured by detector 16 (FIG. 1). Curve "b" is a voltage output from amplifier 20, and shows a decrease $\Delta V_S$ in the scattered light $V_S$, as simultaneously measured by detector 17 (FIG. 1).

By selecting the gains $K_1$ and $K_2$ of amplifiers 19 and 20, respectively, such that $\Delta V_T$ is equal to $\Delta V_S$, the output $V_O$ is nulled. Any further changes in the light readings will now be entirely due to the hemoglobin present in the fraction 12'.

The contribution of the changes in $V_T$ due to the refractive effect of the fluid carrier (plasma) are substantially eliminated whereby small trace amounts of hemoglobin in fraction 12' can be measured.

Figure 4:
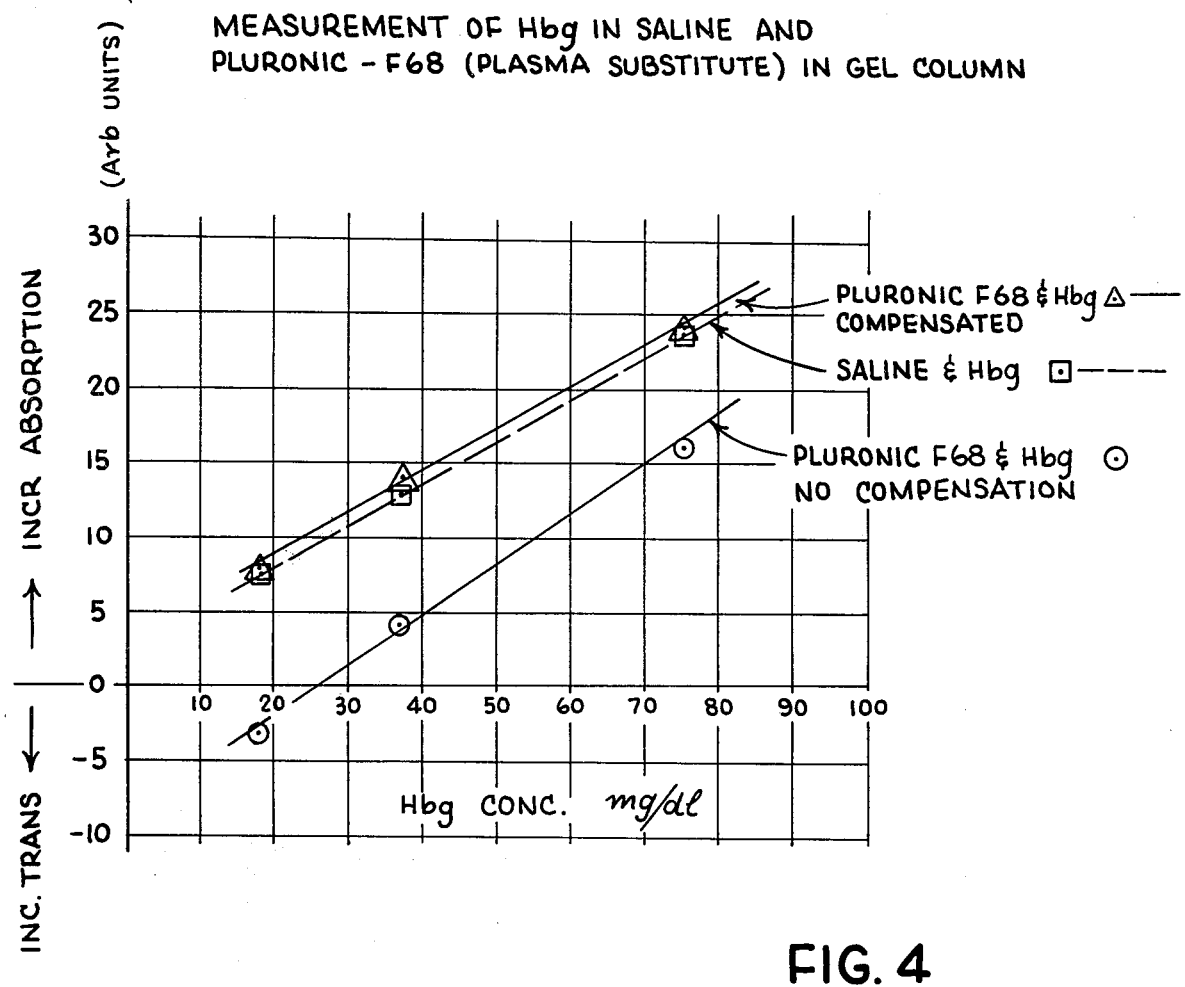
FIG. 4 is a graph of changes in absorption vs. concentration of hemoglobin in solution.

The results of this compensating technique is clearly illustrated in the graph shown in FIG. 4. In this graph, a plasma substitute, Pluronic F-68 (manufactured by BASF-Wyandotte, Polymers, Group, Alkali Sq., Wyandotte, Mich.), was used to adjust the index of refraction of a saline solution to that of blood plasma (1.349). This plasma substitute was then mixed with known amounts of hemoglobin and the mixture was passed through column 10 containing the aforementioned SEPHAROSE gel in a saline solution. Both compensated and uncompensated values were obtained. In addition, known amounts of hemoglobin were mixed with saline to compare these hemoglobin readings with the compensated hemoglobin readings.

As will be observed from the graph in FIG. 4, the compensated hemoglobin (upper solid line) readings closely match within statistical error the readings taken for saline (upper dotted line). This clearly illustrates that the change of the effective refractive index of the column due to the fluid carrier (plasma) has been nullified.

Conversely, the lower solid line of the graph of FIG. 4 shows a lower reading for the hemoglobin when there is no compensation for changes in the effective index of refraction of the column 10 due to the plasma eluant.

While the above invention has been demonstrated for a specific analyte in whole blood, it can be easily realized that the above principles apply to a wide measure of sample materials, both solid, liquid or even gaseous. For example, the above technique may be used to determine the amount of phosphates in detergents. Any number of different analyses for trace quantities of materials in a sample may be accomplished by the aforementioned procedure.

Referring to FIG. 2, a second embodiment of the invention is shown. For the sake of brevity, the same numerical designations have been used for similar elements with those shown in FIG. 1.

As will be observed, only one detector 16 is used in the apparatus of FIG. 2. In this embodiment, the increase $\Delta V_T$ in transmissivity and the decrease $\Delta V_S$ in light scattering are optically nulled. This is accomplished by measuring the light passing through column 10 at a prescribed angle $\theta$ to the directed beam 14, as shown. This angle $\theta$ is determined empirically for each fluid carrier and gel combination, and in the case of plasma, is equal to 145°. At this angle, the measured $\Delta V_T$ is equal to the measured $\Delta V_S$.

Whether the light transmission is electronically nulled as in the case of FIG. 1, or is optically nulled as in the case of FIG. 2, the voltage output $V_O$ in each system is entirely a function of the concentration of the constituent in the particular fraction 12' being measured. The light transmission may either be measured as an absorbance or a transmittance of the transmitted light as is well known in the art.

In some instances, a chromatographic column need not be used for fractionating the sample, but rather other mediums may be used such as disc-gel electrophoresis, diffusion methods, and other gel techniques.

Having described the invention, what is sought to be protected by Letters Patent is presented by the following appended claims.

What is claimed is:

1. A method of determining the concentration of a constituent of a sample within a fluid carrier passing along a medium, the effective index of refraction of said medium being changed due to passage of said carrier therethrough, comprising the steps of:
   (a) obtaining an optical measurement of light that is passed through said medium containing said sample; and
   (b) compensating said optical measurement by substantially nullifying effects due to a change in said effective index of refraction of said medium due to passage of said fluid carrier therethrough which results from said fluid.

2. The method of claim 1, comprising the further step of:
   (c) passing said sample through said medium prior to obtaining said optical measurement.

3. The method of claim 1, wherein said optical measurement is an absorbance measurement.

4. The method of claim 1, wherein said optical measurement is a transmittance measurement.

5. The method of claim 1, wherein said optical measurement of step (a) further comprises the steps of:
   (c) directing a beam of light at said medium along an optical axis;
   (d) measuring said beam of light passing through said medium at two positions in respect to said optical axis so as to obtain first and second light measurements, and
   (e) summing said first and second light measurements to nullify said effects due to said change in said effective index of refraction.

6. The method of claim 5, wherein said measuring step (d) further comprises the step of:
   (e) defining one of said positions along said optical axis.

7. The method of claim 1, wherein said optical measurement step (a) further comprises the step of:
   (c) directing a beam of light at said medium along an optical axis; and, said compensating step (b) further comprises the step of:
   (d) measuring said beam of light passing through said medium at a prescribed angle to said optical axis.

8. The method of claim 1, wherein the respective concentration of more than one constituent in a sample is to be determined, and further wherein steps (a) and (b) are repeated for each constituent.

9. The method of claim 1, further comprising the step of:
   (c) passing said sample along a chromatographic column, so as to fractionate said sample prior to obtaining said optical measurement; and wherein the obtaining of said optical measurement in accordance with step (a) is obtained for a fraction of said sample which contains said constituent.

10. A method of determining the concentration of a constituent in a fluid medium, comprising the steps of:
    (a) passing a fluid medium containing a constituent whose concentration is to be determined along a chromatographic column having an effective refractive index, said fluid medium changing said effective refractive index of said chromatographic column as it passes through said chromatographic column;
    (b) directing a beam of light along an optical axis and through said fluid medium passing along said chromatographic column;
    (c) detecting said beam of light so as to generate an output signal; and
    (d) compensating said output signal to compensate for any changes in said effective refractive index of said column, whereby the compensated output signal is indicative of the concentration of said constituent within said fluid medium.

11. The method of claim 10, wherein said compensating step (d) further comprises the step of:
    (e) measuring said beam of light at a prescribed angle with respect to said optical axis.

12. The method of claim 10, wherein said compensating step (d) further comprises the steps of:
    (f) detecting said beam of light at first and second positions in respect of said optical axis, to obtain first and second light measurements, respectively, so as to generate first and second output signals, respectively; and
    (g) summing said first and second output signals to compensate for any change in said effective refractive index of said column.

13. The method of claim 12, wherein said detecting step (f) further comprises the step of:
    (h) defining one of said positions along said optical axis.

14. The method of claim 10, wherein said fluid medium comprises a plurality of constituents and said method further comprises the step of:
    (e) fractionating said fluid medium to define a plurality of bands as said fluid medium is caused to pass along said chromatographic column, said bands pass, in turn, through said optical axis.

15. The method of claim 10, wherein said chromatographic column comprises an opalescent gel for fractionating said fluid medium.

16. Apparatus for determining the concentration of a constituent within a sample, comprising:
    a chromatographic column for fractionating said sample to obtain a fraction comprising said constituent, said column having an effective refractive index;

optical measuring means for obtaining a measurement of the concentration of said constituent as a function of light passing through said fraction;

compensating means for compensating said measurement to substantially nullify any effect in said measurement due to a change in the effective refractive index of said column during measurement of said concentration of said constitutent.

17. The apparatus of claim 16, wherein said optical measuring means further comprises a source of light, means for passing said light along an optical axis and through said chromatographic column, and first photodetecting means disposed in respect to said optical axis to detect light passing through said fraction.

18. The apparatus of claim 17, wherein said optical measuring means further comprises second photodetecting means disposed in relationship to said first photodetecting means.

19. The apparatus of claim 18, wherein said first detecting means is disposed substantially along said optical axis to detect light transmitted through said column and said second detecting means is disposed substantially at a right angle to said optical axis to detect light scattered by said column.

20. The apparatus of claim 19, wherein said compensating means further comprises a first amplifier connected to said first photodetecting means, a second amplifier connected to said second photodetecting means, and a summing amplifier for receiving output signals from both said first and second amplifiers to generate said measurement, at least one of said first and second amplifiers having a controlled gain to nullify said effect on said measurement.

21. The apparatus of claim 17, wherein said compensating means further comprises means for positioning said first photodetecting means at a prescribed angle with respect to said optical axis.

22. The apparatus of claim 16, wherein said chromatographic column comprises an opalescent gel material.

23. The apparatus of claim 16, wherein said measuring means measures the absorbance of the light beam passing through said chromatographic column.

24. The apparatus of claim 16, wherein said measuring means measures the transmittance of the light beam passing through said chromatographic column.

25. Apparatus for determining the concentration of a constituent in a fluid medium, comprising:
 (a) a chromatographic column having an effective index of refraction;
 (b) means for passing a fluid medium containing a constituent whose concentration is to be determined through said chromatographic column, said fluid medium changing said effective index of refraction of said column;
 (c) means for passing a beam of light through said chromatographic column and said fluid medium;
 (d) means for detecting said beam of light to generate an output signal; and
 (e) means for compensating said output signal in respect of any change in said effective index of refraction of said chromatographic column due to passage of said fluid medium, such that said output signal is substantially a function of the concentration of said constituent within said fluid medium.

26. The apparatus of claim 25, wherein said compensating means further comprises means for positioning said measuring means at a prescribed angle with respect to said directed beam of light.

27. The apparatus of claim 25, wherein said beam of light is directed along an optical axis, and said measuring means further comprises a first and a second measuring means, said first measuring means being substantially disposed along said optical axis, and said second measuring means being substantially disposed at a right angle to said optical axis, and further wherein said compensating means comprises means for summing the measurements of said first and second measuring means.

28. The apparatus of claim 27, wherein said first measuring means comprises a transmission photodetector and said secondl measuring means comprises a scatter photodetector.

29. The apparatus of claim 28, wherein said summing means further comprises a first amplifier connected to said transmission photodetector, a second amplifier connected to said scatter photodetector, and a summing amplifier for receiving output signals from both of said first and second amplifiers, said summing amplifier having an output signal which is substantially a function of the concentration of said constituent in said fluid medium.

* * * * *